US012703831B2

(12) United States Patent
Roberts

(10) Patent No.: US 12,703,831 B2
(45) Date of Patent: Aug. 11, 2026

(54) APPARATUS AND PROCESS FOR REMOVAL OF HEAVY HYDROCARBONS FROM A FEED GAS

(71) Applicant: Honeywell LNG LLC, Wilmington, DE (US)

(72) Inventor: Mark Julian Roberts, Whitehall, PA (US)

(73) Assignee: HONEYWELL LNG LLC, Wilmington, DE (US)

( * ) Notice: Subject to any disclaimer, the term of this patent is extended or adjusted under 35 U.S.C. 154(b) by 370 days.

(21) Appl. No.: 18/211,374

(22) Filed: Jun. 19, 2023

(65) Prior Publication Data

US 2024/0417639 A1 Dec. 19, 2024

(51) Int. Cl.

*C10L 3/10* (2006.01)
*B01D 53/14* (2006.01)
*B01D 53/18* (2006.01)
*C07C 7/11* (2006.01)

(52) U.S. Cl.

CPC .......... *C10L 3/101* (2013.01); *B01D 53/1487* (2013.01); *B01D 53/18* (2013.01); *C07C 7/11* (2013.01); *B01D 2257/7022* (2013.01); *C10L 2290/545* (2013.01); *F25J 2205/30* (2013.01)

(58) Field of Classification Search

CPC ...... F25J 3/0247; F25J 3/0209; F25J 3/04793; F25J 2205/30; F25J 2222/04; C10G 5/06; C10G 2300/25; C10L 2290/10; B01D 53/14; B01D 53/1487

USPC ......... 62/618, 620, 625, 627, 630, 631, 632, 62/635, 636, 638; 585/800; 95/193, 194, 95/187, 188, 186, 223, 180, 179, 178

See application file for complete search history.

(56) References Cited

U.S. PATENT DOCUMENTS 2,888,807 A * 6/1959 Bocquet ................. F25J 3/0266 62/929
3,192,732 A * 7/1965 Cahn ...................... F25J 3/0242 62/110

(Continued)

FOREIGN PATENT DOCUMENTS

WO 2018055264 A1 3/2018
WO 2021055021 A1 3/2021

OTHER PUBLICATIONS

European Search Report for application EP 24183149, dated Oct. 28, 2024, HOY20049EP, 9 pages.

(Continued)

*Primary Examiner* — Melvin C. Mayes

(74) *Attorney, Agent, or Firm* — CANTOR COLBURN LLP

(57) ABSTRACT

An apparatus and process for removal of heavy hydrocarbons (e.g., hydrocarbons that include five or more carbons such as pentane and hexane, etc.) from a feed (e.g., a feed comprised of methane and impurities) can include a scrub column and a stabilizer column arranged so that a portion of a first stream output from the stabilizer column is fed to the scrubber column to function as a reflux stream. Embodiments are provided in which the scrub column produces a stream comprising mostly methane (e.g. over 85 mole percent methane) and reduced heavy hydrocarbons so that reduced operational costs and improved operational flexibility can be realized in downstream natural gas liquefaction operations.

16 Claims, 2 Drawing Sheets

(56) References Cited

U.S. PATENT DOCUMENTS 3,313,724 A * 4/1967 Kniel ..................... F25J 3/0247 203/84
3,542,892 A * 11/1970 Briggs ..................... C07C 7/00 585/502
3,967,937 A * 7/1976 Hobbs ..................... G05B 13/02 700/75
4,033,617 A * 7/1977 Cocuzza ............. C07D 301/32 203/75
4,120,667 A * 10/1978 Gettert ..................... C01C 1/12 95/183
4,332,596 A * 6/1982 Ranke ................ B01D 53/1468 95/8
4,462,814 A * 7/1984 Holmes ................... C01B 32/50 62/929
4,512,782 A * 4/1985 Bauer ...................... C07C 7/04 95/177
4,617,039 A 10/1986 Buck
4,695,672 A * 9/1987 Bunting ................... C10G 5/04 95/194
4,696,688 A * 9/1987 Mehra ...................... C10L 3/10 62/635
4,705,549 A 11/1987 Sapper
4,707,171 A 11/1987 Bauer
RE32,600 E * 2/1988 Ryan ...................... F25J 3/0242 62/929
4,741,884 A * 5/1988 Carter ................ B01D 53/1406 422/171
4,883,515 A * 11/1989 Mehra ...................... C10L 3/10 62/632
4,897,098 A * 1/1990 Pate ......................... C07C 7/04 62/630
5,035,732 A * 7/1991 McCue, Jr. ............ F25J 3/0219 62/627
5,114,450 A * 5/1992 Paradowski ........... F25J 3/0233 62/635
5,253,479 A * 10/1993 Di Cintio ............... F25J 3/0242 62/631
5,673,571 A * 10/1997 Manley .................. F25J 3/0209 62/631
5,685,170 A * 11/1997 Sorensen ........... B01D 53/1418 62/635
5,771,712 A * 6/1998 Campbell .............. F25J 3/0242 62/621
5,799,507 A * 9/1998 Wilkinson ............. F25J 3/0233 62/619
5,953,936 A * 9/1999 Agrawal ................ F25J 3/0295 62/643
5,954,924 A * 9/1999 Art ......................... C07C 15/46 585/800
6,340,429 B1 * 1/2002 Minkkinen ............ C10G 70/00 585/650
6,358,399 B1 * 3/2002 Minkkinen ............ C10G 70/02 585/650
6,401,486 B1 * 6/2002 Lee ........................ F25J 1/0035 62/623
6,483,000 B2 * 11/2002 Becker ................ C07C 7/14891 585/800
6,516,631 B1 * 2/2003 Trebble .................. F25J 3/0209 62/631
6,581,410 B1 6/2003 Johnson et al.
6,585,807 B2 * 7/2003 Umino ..................... C01C 1/12 95/193
6,658,893 B1 12/2003 Mealey
6,712,880 B2 3/2004 Foglietta et al.
6,742,358 B2 6/2004 Wilkinson et al.
7,377,127 B2 * 5/2008 Mak ....................... F25J 3/0209 62/635
7,458,232 B2 12/2008 Paradowski
7,842,847 B2 * 11/2010 Panditrao ................. C10G 7/00 62/620
8,182,654 B2 * 5/2012 Sechrist ................... B01D 3/14 203/99
8,287,626 B2 * 10/2012 Hoang-Dinh ...... B01D 53/1462 95/193
8,470,077 B2 * 6/2013 Dube ................. B01D 53/1425 95/193
8,673,062 B2 * 3/2014 Menzel ............. B01D 53/1418 95/193
8,845,790 B2 * 9/2014 Leister .............. B01D 53/1425 95/193
10,451,344 B2 10/2019 Mak
11,339,339 B1 * 5/2022 Nouri ...................... C10L 3/104
11,499,775 B2 11/2022 Roberts et al.
2002/0166336 A1 11/2002 Wilkinson et al.
2006/0021379 A1 * 2/2006 Ronczy .................. F25J 3/0238 62/620
2006/0277943 A1 * 12/2006 Yokohata .................. C07C 7/04 62/620
2007/0062216 A1 * 3/2007 Mak ....................... F25J 3/0242 62/620
2007/0101732 A1 * 5/2007 Mak ....................... F25J 3/0233 62/620
2007/0157663 A1 * 7/2007 Mak ....................... F25J 1/0022 62/620
2007/0240450 A1 * 10/2007 Mak ....................... F25J 3/0209 62/626
2008/0141712 A1 * 6/2008 Verma .................... F25J 3/0242 62/620
2008/0264100 A1 * 10/2008 Mak ....................... F25J 3/0238 62/621
2009/0165498 A1 * 7/2009 Mak .......................... C10L 3/12 62/626
2010/0206003 A1 * 8/2010 Mak ....................... F25J 3/0242 62/630
2012/0000244 A1 * 1/2012 Sechrist ................. B01D 3/007 62/620
2012/0000245 A1 * 1/2012 Currence ............... F25J 3/0242 62/620
2012/0324943 A1 * 12/2012 Butts ...................... F25J 3/0233 62/630
2013/0102828 A1 * 4/2013 Knudsen .............. B01J 31/4015 585/800
2013/0213088 A1 * 8/2013 Stylianou ............... F25J 3/0242 62/620
2014/0007616 A1 * 1/2014 Mak ....................... F25J 3/0233 62/620
2015/0114035 A1 * 4/2015 Briglia ................... F25J 3/0233 62/620
2015/0159939 A1 * 6/2015 Valencia ................ F25J 3/0209 62/618
2015/0184932 A1 * 7/2015 Higginbotham ......... C10G 7/00 62/620
2015/0219394 A1 * 8/2015 Russeff .................. C10G 65/00 62/620
2015/0267137 A1 * 9/2015 Sapper ..................... F25J 3/061 62/620
2016/0216030 A1 7/2016 Truong et al.
2018/0266757 A1 * 9/2018 Embry .................... C10L 3/101
2018/0273858 A1 * 9/2018 Davies ..................... C10G 7/00
2019/0128600 A1 * 5/2019 Yamamori ............. F25J 3/0233
2019/0143261 A1 * 5/2019 Mabrouk ........... B01D 53/1475 95/180
2019/0271503 A1 * 9/2019 Terrien .................... C10L 3/101
2020/0191477 A1 * 6/2020 Mak ....................... F25J 1/0022
2021/0086099 A1 * 3/2021 Liu ........................ F25J 1/0072
2021/0088275 A1 3/2021 Liu et al.
2021/0116173 A1 4/2021 Chan et al.
2022/0178609 A1 6/2022 Horne et al.
2022/0364005 A1 * 11/2022 Praderio ................ F25J 3/0233
2024/0417639 A1 * 12/2024 Roberts .................. F25J 3/0209

OTHER PUBLICATIONS

R.N. Pitman, et al., "Next Generation Processes for NGL/LPG Recovery", 77th Annual Convention of the Gas Processors Association, 1998, 1-13.

(56) References Cited

OTHER PUBLICATIONS

Japanese OA for application JP 2024-094801, Issued May 27, 2025 in HOY20049JP, 3 pages.

* cited by examiner

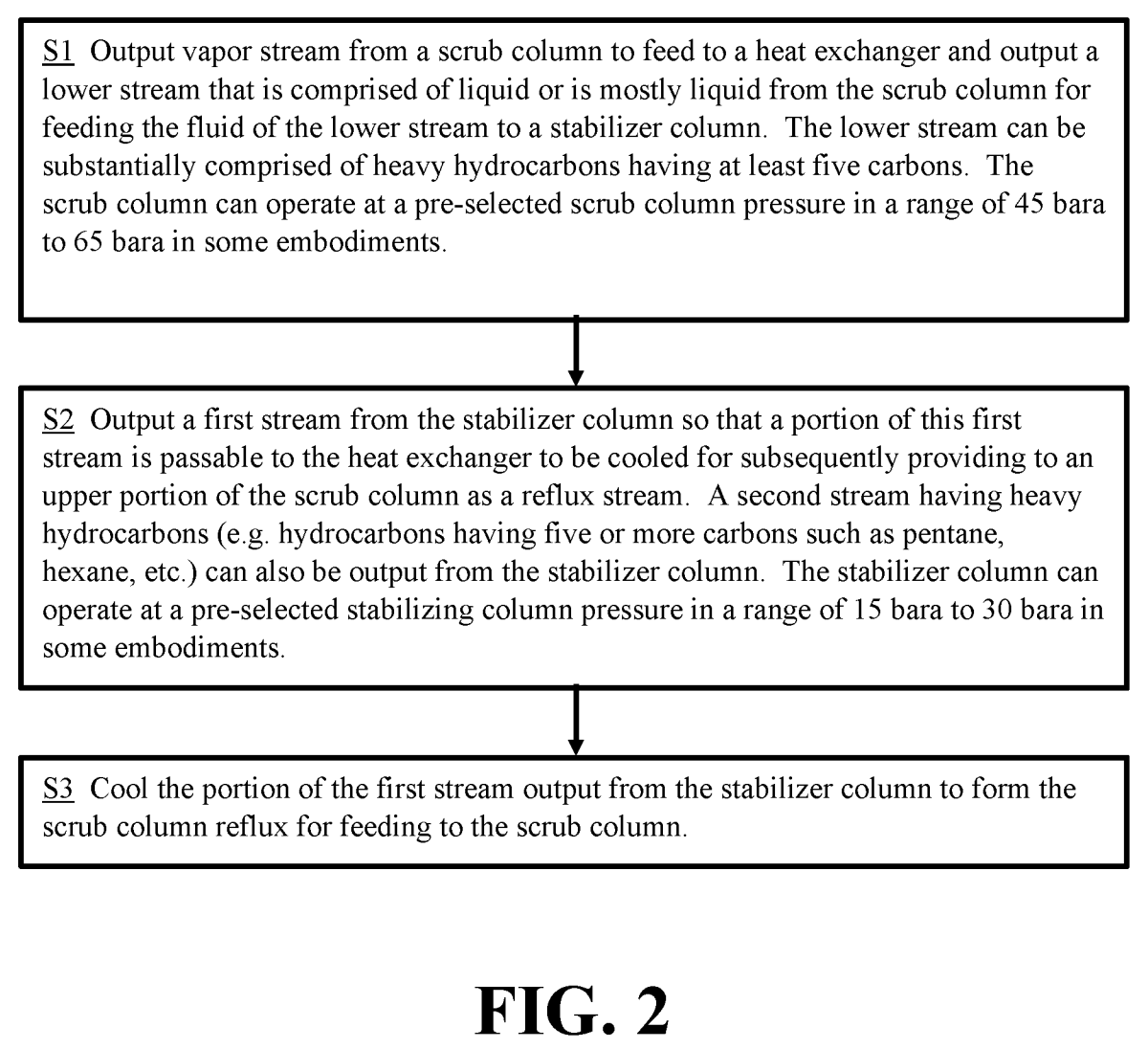

S1 Output vapor stream from a scrub column to feed to a heat exchanger and output a lower stream that is comprised of liquid or is mostly liquid from the scrub column for feeding the fluid of the lower stream to a stabilizer column. The lower stream can be substantially comprised of heavy hydrocarbons having at least five carbons. The scrub column can operate at a pre-selected scrub column pressure in a range of 45 bara to 65 bara in some embodiments.

S2 Output a first stream from the stabilizer column so that a portion of this first stream is passable to the heat exchanger to be cooled for subsequently providing to an upper portion of the scrub column as a reflux stream. A second stream having heavy hydrocarbons (e.g. hydrocarbons having five or more carbons such as pentane, hexane, etc.) can also be output from the stabilizer column. The stabilizer column can operate at a pre-selected stabilizing column pressure in a range of 15 bara to 30 bara in some embodiments.

S3 Cool the portion of the first stream output from the stabilizer column to form the scrub column reflux for feeding to the scrub column.

FIG. 2

APPARATUS AND PROCESS FOR REMOVAL OF HEAVY HYDROCARBONS FROM A FEED GAS

FIELD

The present innovation relates to processes and systems for treating gas feeds that comprise methane (e.g., natural gas) to remove impurities from the feed (e.g., remove heavy hydrocarbons having 5 or more carbons within the gas feed, etc.).

BACKGROUND

Liquified natural gas (LNG) includes methane ($CH_4$) that is cooled and liquified so it is in a liquid state. Example of systems and processes involving LNG can be appreciated from U.S. Patent Application Publication Nos. 2022/0178609 and 2016/0216030 and U.S. Pat. No. 11,499,775.

SUMMARY

Cryogenic natural gas liquid (NGL) recovery plants and LNG plants are often configured to remove some heavier hydrocarbon components from the natural gas feed that would freeze during the cryogenic process to liquefy methane in the feed. Such conventional systems often provide a feed comprising methane for liquefaction processing that can require significant compression, which can incur a substantial operational cost to the liquefaction processing and also limit how such liquefaction processing can be arranged and configured. Described herein are embodiments of a process for feed gas treatment and an apparatus for feed gas treatment that can permit heavy hydrocarbons to be removed from a feed more effectively while also reducing operational costs and providing improved operational flexibility for downstream liquid natural gas liquefaction processing for the feed.

Embodiments of the apparatus and process described herein can be configured so that a scrub column can be operated at a pre-selected pressure that can be selected independently from the refrigeration demand of pre-cooling via a feed pre-cooling heat exchanger. Embodiments can be adapted so that a vapor stream output from the scrub column that comprises mostly methane can be fed to a liquefaction apparatus (e.g. a liquefier, etc.) at an elevated pressure, which can decrease power requirements for downstream liquefaction of the output vapor stream. Embodiments of the process and apparatus can be configured so that the feed is at an ambient temperature (e.g. between 0° C. and 40° C., between 20° C. and 40° C., etc.).

In some embodiments, a feed comprising methane as well as heavy hydrocarbon impurities is fed to a heat exchanger before being fed to the scrub column. The scrub column can be configured to output a first vapor stream comprising methane and a second stream having heavy hydrocarbons. The second stream can be fed to a stabilizer column, which can be configured to output a first stream for forming a reflux stream that can be fed to the scrub column and a second stream having heavy hydrocarbons for separation of the heavy hydrocarbons from the feed. The first vapor stream comprising methane can be passed through the heat exchanger to help cool and/or form the reflux stream provided via the stabilizer column before the formed reflux stream is fed to the scrub column.

In some embodiments, a reflux accumulator vessel (e.g. a reflux accumulator drum) can be provided between the heat exchanger and the scrub column to retain the formed reflux stream so that a sufficient supply of reflux can be provided to a scrub column pump used to provide reflux to the scrub column. In some embodiments the reflux accumulator vessel can be positioned and configured to help protect the scrub pump to avoid cavitating the pump. In the same or other embodiments, the stabilizer column and scrub column can be arranged and configured so that the scrub column can operate at a pressure within a range of 45 bara to 65 bara and the stabilizer column can operate at a pressure within a range of 15 bara to 30 bara. In other embodiments, other pressure ranges for the stabilizer column and/or scrub column can also be utilized such that the stabilizer column operates at a different operational pressure range that is lower than an operational pressure range of the scrub column. The vapor stream output from the scrub column is comprised mostly of methane (e.g. between 80 mole percent (mol %) methane and 95 mol % methane, at least 85 mol % methane and less than 100 mol % methane, at least 75 mol % methane, at least 90 mol % methane, etc.) and can be at an elevated pressure.

In a first aspect, an apparatus for removal of heavy hydrocarbon impurities from a feed comprising methane gas and heavy hydrocarbons having at least five carbon atoms is provided. The apparatus can include a scrub column positioned and configured to receive the feed and output a first scrub column stream and a second scrub column stream. The second scrub column stream can comprise the heavy hydrocarbons. The apparatus can also include a stabilizer column positioned downstream of the scrub column to receive the second scrub column stream. The stabilizer column can be configured to output a first stabilizer column stream and a second stabilizer column stream. The second column stabilizer stream can comprise the heavy hydrocarbons. The scrub column can be configured such that a portion of the first stabilizer column stream is fed to the scrub column to provide scrub column reflux.

In some embodiments, the scrub column can be operated at an elevated pressure to provide a treated feed gas at an elevated pressure to provide the treated feed to a downstream LNG or NGL plant so that improved operational flexibility and a reduced compression duty is required by the downstream plant. Some embodiments may be integrated into an LNG plant or NGL plant or as a separate pretreatment facility that may supply treated feed for such a plant.

Some embodiments can be adapted so that an expander is not utilized for expansion of the feed to the scrub column. Some embodiments can be configured so that the operational pressure range of the scrub column is higher than the operational pressure range of the stabilizer column.

In a second aspect, the apparatus can include a reflux accumulator vessel configured to receive the portion of the first stabilizer stream that is fed to the scrub column, store the scrub column reflux, and feed the scrub column reflux to the scrub column.

In a third aspect, the apparatus can include a heat exchanger positioned to cool at least a portion of the feed before the feed is fed to the scrub column, receive the first scrub column stream from the scrub column, and/or cool the portion of the first stabilizer column stream that may be fed to the scrub column to form a scrub column reflux stream which may be fed to the reflux accumulator vessel. For example, a heat exchanger can be positioned to cool a first portion of the feed before the feed is fed to the scrub column, receive the first scrub column stream from the scrub column, and cool the portion of the first stabilizer column stream that is fed to the scrub column to form a scrub column reflux stream which is fed to the scrub column to provide scrub column reflux.

In a fourth aspect, the scrub column of the apparatus can be positioned so that a second portion of the feed or a third portion of the feed may be passed through a side reboiler for cooling that portion of the feed and heating liquid from the scrub column received by the side reboiler to form a stripping vapor. The side reboiler can be positioned to output the stripping vapor to the scrub column. The side reboiler can be positioned and arranged so that the second portion of the feed or the third portion of the feed output from the side reboiler may be fed to the scrub column. For instance, in some embodiments a heat exchanger and the scrub column can be positioned such that the second portion of the feed or the third portion of the feed output from the side reboiler is combined with a first portion of the feed and fed to the scrub column.

In a fifth aspect, the apparatus can include a pump positioned to drive a flow of the scrub column reflux to the scrub column. For example, embodiments can include a reflux accumulator vessel positioned to receive the portion of the first stabilizer stream that is fed to the scrub column, store the scrub column reflux, and feed the scrub column reflux to the scrub column. Such embodiments can also include a pump positioned to drive a flow of the scrub column reflux from the reflux accumulator vessel to the scrub column. In such embodiments, the stabilizer column can be configured to operate at a pre-selected stabilizer column operational pressure range and the scrub column can be configured to operate at a pre-selected scrub column operational pressure range that is greater than the pre-selected stabilizer column operational pressure range.

In a sixth aspect, the apparatus can include a phase separator positioned to receive the first stabilizer column stream and output a vapor stream and a liquid stream. The phase separator can be positioned so that a portion of the liquid stream and the vapor stream can be fed to the scrub column to form the scrub column reflux for providing reflux to the scrub column.

In some embodiments, a heat exchanger can be positioned to receive the vapor stream from the phase separator and a first portion of the liquid stream from the phase separator. The portion of the first stabilizer column stream that is fed to the scrub column as scrub column reflux can include the vapor stream from the phase separator and the first portion of the liquid stream from the phase separator. The heat exchanger can be configured and positioned to cool a first portion of the feed before the feed is fed to the scrub column and cool the vapor stream and the first portion of the liquid stream to form a scrub column reflux stream for providing the scrub column reflux for feeding to the scrub column.

Also, in some embodiments a reflux accumulator vessel can be positioned to receive the scrub column reflux stream output from the heat exchanger, store the scrub column reflux, and feed the scrub column reflux to the scrub column and/or a pump positioned to drive a flow of the scrub column reflux from the reflux accumulator vessel to the scrub column. In such embodiments or in other embodiments, the stabilizer column can be configured to operate at a pre-selected stabilizer column operational pressure range and the scrub column can be configured to operate at a pre-selected scrub column operational pressure range that is greater than the pre-selected stabilizer column operational pressure range.

In a seventh aspect, the apparatus of the first aspect can include one or more features of the second aspect, third aspect, fourth aspect, fifth aspect and/or sixth aspect. It should therefore be appreciated that embodiments of the apparatus can include other elements or features of different exemplary embodiments. For example, embodiments can include one or more exemplary features of the exemplary embodiments discussed herein.

In an eighth aspect, a process for treating a feed gas comprising methane and heavy hydrocarbons having at least five carbon atoms is provided. Embodiments of the process can include providing a feed to a scrub column operating at a pre-selected scrub column operational pressure range and outputting a first scrub column stream and a second scrub column stream from the scrub column. The second scrub column stream can comprise the heavy hydrocarbons.

The process can also include feeding the second scrub column stream to a stabilizer column operating at a pre-selected stabilizer column operational pressure range for outputting a first stabilizer column stream and a second stabilizer column stream. The second stabilizer column stream can comprise the heavy hydrocarbons.

The process can also include feeding a portion of the first stabilizer column stream to the scrub column to provide scrub column reflux to the scrub column.

Embodiments of the apparatus can be configured to implement or utilize an embodiment of the process. Embodiments of the process can be configured so that a treated feed can be provided as the first scrub column stream at an elevated pressure to a suitable downstream plant to reduce the compression duty needed at the downstream plant and provide improved operational flexibility. The downstream plant can be, for example, an LNG plant or NGL plant.

In a ninth aspect, the process can include additional steps. For example, the process can also include feeding the first stabilizer column stream to a phase separator to form a vapor stream and a liquid stream, feeding the vapor stream and a portion of the liquid stream to a heat exchanger for forming the scrub column reflux, feeding the scrub column reflux output from the heat exchanger to a reflux accumulator vessel, and feeding the scrub column reflux from the reflux accumulator vessel to an upper section of the scrub column. Also, the process can include feeding the first scrub column stream to the heat exchanger as a cooling medium to facilitate cooling of the vapor stream and the portion of the liquid stream fed to the heat exchanger to form the scrub column reflux.

In a tenth aspect, the pre-selected scrub column operational pressure range can be higher than the pre-selected stabilizer column operational pressure range. For example, the pre-selected scrub column operational pressure range can be between 45 bara and 65 bara and the pre-selected stabilizer column operational pressure range can be between 15 bara and 30 bara.

In an eleventh aspect, the process can include splitting the feed into different portions. For example, the process can include splitting the feed into a first portion and a second portion and feeding the first portion to a heat exchanger positioned upstream of the scrub column prior to mixing the first portion with the second portion and feeding the combined feed to the scrub column.

As another example, the process can include splitting the feed into a first portion, a second portion, and a third portion, feeding the first portion to a heat exchanger positioned upstream of the scrub column prior to mixing the first portion with the second portion, and feeding the combined feed to the scrub column, and feeding the third portion to a lower section of the scrub column.

As yet another example, the process can include splitting the feed into a first portion and a second portion, feeding the first portion to a heat exchanger positioned upstream of the scrub column, feeding the first portion to the scrub column, and feeding the second portion to a lower section of the scrub column.

As yet another example, the process can include splitting the feed into a first portion, a second portion, and a third portion, feeding the first portion to a heat exchanger positioned upstream of the scrub column, mixing the first portion with the second portion and feeding the combined feed to the scrub column, and feeding the third portion to a side reboiler for forming a stripping vapor to feed to the scrub column prior to the third portion being fed to the scrub column.

Embodiments of the process can also include other steps related to processing of different portions of the split feed. For example, the process can also include mixing the third portion with the second portion and/or the first portion before the first portion, second portion, and third portion of the feed are fed to the scrub column.

In a twelfth aspect, the process of the eighth aspect can include one or more features of the ninth aspect, tenth aspect, and/or eleventh aspect. It should therefore be appreciated that embodiments of the process can include other elements or features of different exemplary embodiments. For example, embodiments can include one or more exemplary features of the exemplary embodiments discussed herein.

It should be appreciated that embodiments of the process and apparatus can utilize various conduit arrangements and process control elements. The embodiments may utilize sensors (e.g., pressure sensors, temperature sensors, flow rate sensors, concentration sensors, etc.), controllers, valves, piping, and other process control elements. Some embodiments can utilize an automated process control system and/or a distributed control system (DCS), for example. Various conduit arrangements and process control systems can be utilized to meet a particular set of design criteria.

Other details, objects, and advantages of the present invention, including processes for treating gas feeds that comprise methane (e.g., natural gas) to remove impurities from the feed, apparatuses for treating gas feeds that comprise natural gas to remove impurities from the feed gas, systems for treating gas feeds that comprise methane to remove impurities from the feed, and methods of making and using the same will become apparent from the following detailed description of certain exemplary embodiments.

BRIEF DESCRIPTION OF THE DRAWINGS

Exemplary embodiments of the present invention, including processes for treating gas feeds that comprise methane (e.g., natural gas) to remove impurities (e.g. heavy hydrocarbons) from the feed, apparatuses for treating gas feeds that comprise natural gas to remove impurities from the feed gas, systems for treating gas feeds that comprise methane to remove impurities from the feed, and methods of making and using the same are shown in the drawings included herewith. It should be understood that like reference characters used in the drawings may identify like components.

FIG. 1 also illustrates a first exemplary embodiment of a process for treating a gas feed that comprises methane to remove impurities from the feed gas. The impurities present in the feed gas to be treated can include heavy hydrocarbons (e.g. hydrocarbons having five or more carbons such as, for example, pentane, hexane, heptane, octane, etc.).

FIG. 2 is a flow chart illustrating an exemplary embodiment of a process for treating a feed gas that comprises methane to remove impurities from the feed gas. Exemplary embodiments of the apparatus shown in FIG. 1 can be adapted to implement the exemplary embodiment of the process shown in FIG. 2.

DETAILED DESCRIPTION

Figure 1:
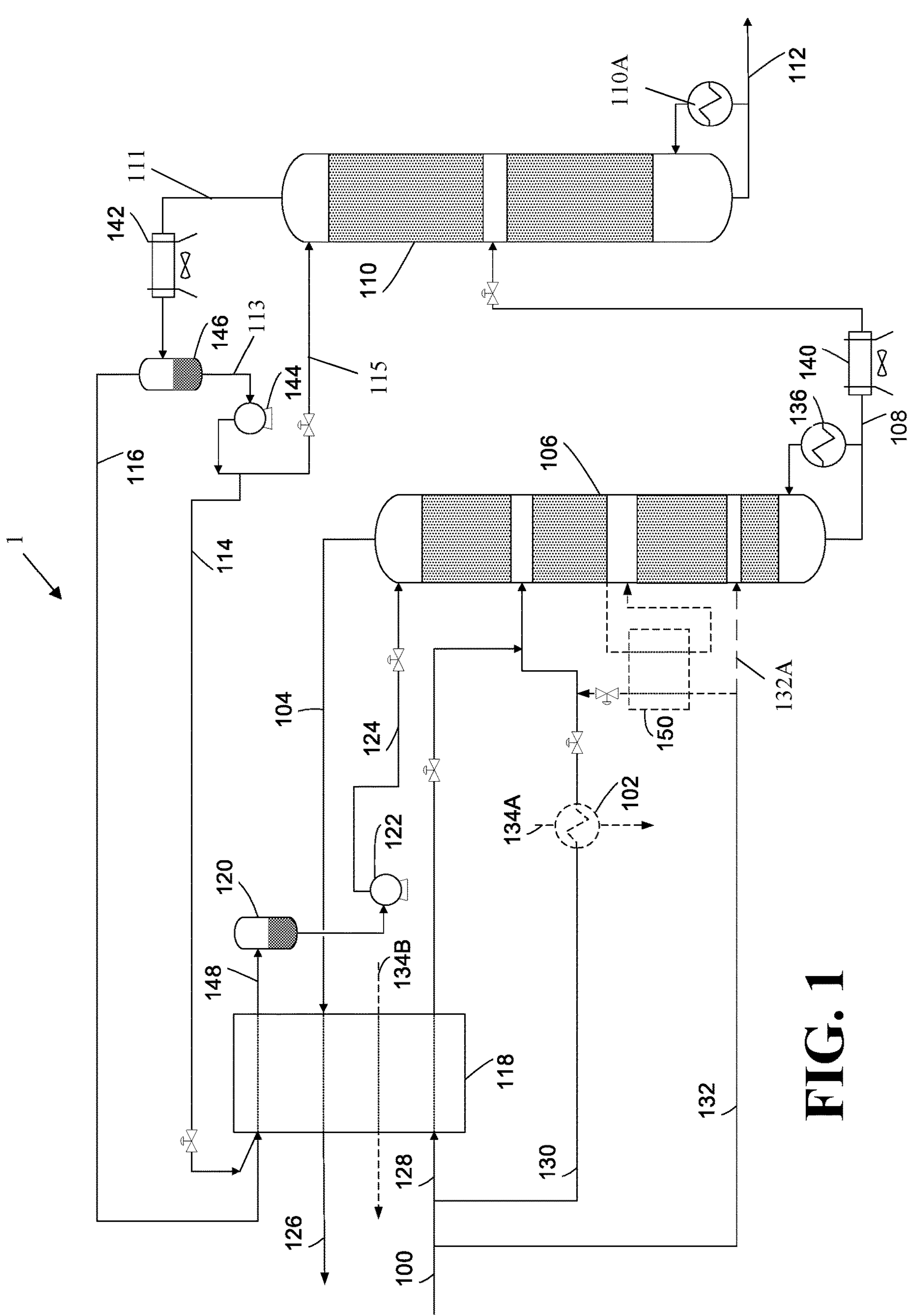
FIG. 1 is a block diagram of a first exemplary embodiment of an apparatus for treating a gas feed that comprises methane to remove impurities from the feed gas.

FIG. 1 illustrates exemplary embodiments of an apparatus 1 for treating one or more feeds that comprise methane to remove impurities from the feed. The impurities to be removed can include heavy hydrocarbons that have five or more carbon atoms (e.g. pentane, hexane, heptane, benzene, etc.). These exemplary embodiments of the apparatus 1 can utilize an exemplary embodiment of a process for treating one or more gas feeds that comprise methane to remove impurities from the feed. Examples of such processes can be appreciated from FIGS. 1 and 2.

A feed 100 can be an entirely gaseous feed that is provided at an initial feed temperature. The initial feed temperature for the feed 100 can be ambient temperature (e.g. between 0° C. and 40° C., around 25° C., between −5° C. and 40° C., etc.). The feed can be provided via a natural gas pipeline or other source of feed 100 for embodiments in which the feed is comprised of natural gas (e.g. methane, $CH_4$). The feed 100 can also include impurities that can include ethane, propane, butane, and heavy hydrocarbons having five or more carbon atoms (e.g. C5+ hydrocarbons such as pentane, isopentane, hexane, benzene, heptane, toluene, octane, etc.). The feed 100 may also include trace amounts of other gases, such as nitrogen and carbon dioxide.

In some embodiments, the feed 100 can be comprised mostly of methane. For example, the feed can have between 75 mole percent (mol %) and 100 mol % methane, between 1 mol % and 8 mol % ethane, between 0.2 mol % and 3 mol % ethane, and between 0.01 mol % and 0.5 mol % butane in some embodiments, as well as having between 1 mol % and greater than 0 mol % amounts of heavy hydrocarbons having five or more carbon atoms. The feed can also include between 0 mol % and 3 mol % nitrogen and between 0 mol % and 0.1 mol % carbon dioxide. In some embodiments, the feed can also include hydrogen gas and/or other constituents.

The feed 100 can be split into multiple portions upstream of a heat exchanger 118 and the different portions routed to a scrub column 106 and/or the heat exchanger 118. For example, the feed 100 can be split into a first portion 128 that is passed through the heat exchanger 118 to undergo cooling therein, a second portion 130 that can be split from the first portion upstream of the heat exchanger 118 and passed to the scrub column 106, and a third portion 132 that can be fed to the scrub column at a bottom section or lower section of the scrub column 106 as a lower section feed portion 132A.

In alternative implementations (as shown in broken line in FIG. 1), the third portion 132 can be passed through a side reboiler 150 to function as a heating medium to indirectly heat a fluid of the scrub column 106 fed to the side reboiler 150 so that the fluid can be vaporized and fed from the side reboiler 150 to the scrub column 106 as a vapor (shown in broken line in FIG. 1). In the event the third portion is passed through the side reboiler 150, the third portion can be output from the side reboiler 150 and either mixed with the second portion 130 and/or first portion 128 for feeding to the scrub column 106 or can be output from the side reboiler 150 and fed from the side reboiler 150 to the scrub column 106.

The first, second, and third portions of the feed 100 can be split to include different flow rates of the feed. For example, the first portion can be the largest portion of the first, second, and third portions and the second portion may be smaller or larger than the third portion. For instance, the first portion can be between 50% and 80% of the feed 100. The second portion 130 can be between 45% and 5% of the feed 100 and the third portion 132 can be between 45% and 5% of the feed.

The first portion 128 can be passed through the heat exchanger 118 to be cooled to a pre-selected first portion cooled temperature that is within a pre-selected first portion scrub column feed temperature range. An example of the pre-selected first portion scrub column feed temperature range can be between −20° C. and −50° C. or another suitable temperature range. After the cooled first portion 128 is output from the heat exchanger 118, it can be fed to an upper section or intermediate section of the scrub column 106. In some embodiments, the first portion 128 can be mixed with the second portion 130 before the mixed first and second portions are fed to the scrub column 106. In other embodiments, the first portion 128 can be fed to the scrub column 106 via a separate feed conduit and the second portion 130 can also be fed to the scrub column 106 via a separate feed conduit.

The second portion 130 can be split from the first portion 128 and subsequently fed to an upper section or intermediate section of the scrub column 106 via a second portion feed conduit connected between a feed conduit and the scrub column 106. The second portion 130 can be optionally cooled via a cooler 102 to a pre-selected second portion scrub column feed temperature within a pre-selected second portion scrub column feed temperature range before the second portion 130 is fed to the scrub column 106. An example of the pre-selected second portion scrub column feed temperature range can be between −15° C. and −45° C. or another suitable temperature range.

The second portion cooler 102 that can be positioned to cool the second portion (as shown in broken line in FIG. 1) can be a chiller, a mechanical chiller, or other type of cooler that can utilize a flow of refrigerant 134A as a cooling medium for cooling the second portion 130. This refrigerant 134A can be, for example, liquid propane from a downstream LNG plant, a mixed refrigerant from a downstream LNG plant, a chilled gaseous methane or nitrogen stream from a downstream LNG plant or other type of refrigerant or cooling medium that may be output from a downstream liquefier or LNG plant, or can be another process gas from another process element (e.g. a waste stream from an air separation unit, etc.).

In other arrangements, the second portion cooler 102 may not be utilized. For example, the cooling from the heat exchanger 118 that is provided to the first portion 128 that is subsequently mixed with the second portion 130 can be sufficient to also sufficiently cool the second portion 130 so that the mixed feed of the first and second portion 128 and 130 can be fed to the scrub column 106 at a suitable scrub column feed temperature. For instance, a cooling medium flow 134B (shown in broken line in FIG. 1) can be fed to the heat exchanger 118 as a cooling medium to help sufficiently cool the first portion 128 via the heat exchanger 118 so that the mixed flow of the first portion 128 and second portion 130 that is formed downstream of the heat exchanger 118 is at a suitable feed temperature for the scrub column 106.

Alternatively, cooling can be provided via the cooling medium flow 134B and/or first scrub column stream 104 fed to the heat exchanger 118 so that no second portion 130 of the feed is formed and instead only the first portion 128 and the third portion 132 are formed. In such an arrangement in which second portion 130 is not formed, the third portion 132 can be considered a second portion of the feed 100 and can be fed to the lower section of the scrub column as lower section feed portion 132A or fed to a side reboiler 150 before being fed to the scrub column 106 and/or being mixed with the first portion 128 for being fed to the scrub column 106.

The flow of cooling medium 134B (shown in broken line in FIG. 1) can be, for example, liquid propane from an LNG plant or other type of refrigerant or cooling medium that may be output from a downstream liquefier or LNG plant or can be another process gas from another process element (e.g. a waste stream from an air separation unit, etc.). For example, the flow of cooling medium 134B can be liquid propane from a downstream LNG plant, a mixed refrigerant from a downstream LNG plant, a chilled gaseous methane or nitrogen stream from a downstream LNG plant or other type of refrigerant or cooling medium that may be output from a downstream liquefier or LNG plant or can be another process gas from another process element (e.g. a waste stream from an air separation unit, etc.). Other embodiments can utilize yet other refrigerant sources as the cooling medium 134B as well.

Embodiments that may use the cooling medium 134B from an external source (e.g. other plant process, liquefier, etc.) can be adapted to provide cooling without reducing or lowering the scrub column pressure. This can permit the scrub column 106 to be operated at a higher pressure to provide the treated stream 126 at an elevated pressure, which in turn can help avoid the use of an expander (e.g. expansion of feed 100) and the reduction in pressure associated with use of an expander.

The scrub column 106 can receive the first, second, and third portions 128, 130, and 132 of the feed 100, scrub the feed to remove heavy hydrocarbons from the feed 100, and output a first scrub column stream 104, which can also be considered a treated feed stream 104 or a scrub column vapor stream 104. The first scrub column stream 104 can be output from the top of the scrub column or adjacent to an upper section of the scrub column 106 as a vapor stream that is comprised entirely of gas. The scrub column 106 can also output a second scrub column stream 108 at the bottom or adjacent to bottom of the scrub column (e.g. at a lower section of the scrub column 106).

The scrub column 106 can include a reboiler 136 positioned to strip methane and ethane from a second scrub column stream 108 of the scrub column 106 or bottom of the scrub column 106 so that the stripped methane and ethane can be returned to the scrub column 106 and the second stream 108 can be output as a second scrub column stream 108 comprising mostly heavy hydrocarbons with a relatively small amount of methane and ethane therein. In some embodiments, the second scrub column stream 108 can include more than 0 mol % methane and less than 20 mol % methane, and more than 0 mol % ethane and less than 20 mol % methane. The remaining portion of the second scrub column stream 108 can include heavy hydrocarbons, propane, butane, and other impurities from the feed 100. In some embodiments, the second scrub column stream 108 can comprise between 30 mol % and 50 mol % heavy hydrocarbons or between 20 mol % and 40 mol % heavy hydrocarbons.

As noted above, the scrub column 106 can also include an optional side reboiler 150, which can utilize the third portion 132 as a heating medium to vaporize condensate or liquid from a lower section of the scrub column 106 before being fed back to the scrub column 106 as a stripping vapor for use therein.

The scrub column 106 can be arranged and configured so that it can operate within a pre-selected scrub column pressure range. This pressure range can be selected to provide the first scrub column stream 104 at an elevated pressure. In some embodiments, the pre-selected scrub column pressure range can be between 45 bara and 65 bara. Other embodiments may utilize another suitable pressure range for the pre-selected scrub column pressure range to meet a particular set of design criteria.

The second scrub column stream 108 can be output from the scrub column 106 and fed to a stabilizer column feed cooler 140. The stabilizer column feed cooler 140 can be positioned between the scrub column 106 and the stabilizer column 110 to cool the second scrub column stream 108 to a pre-selected stabilizer column feed temperature. The stabilizer column feed cooler 140 can be a chiller or heat exchanger that may utilize an ambient air or chilling water cooling medium or other suitable cooling medium for cooling the second scrub column stream 108 to the pre-selected stabilizer column feed temperature. In some embodiments, this temperature can be within a temperature range of 0° C. to 30° C. or −5° C. to 40° C.

The second scrub column stream 108 can be fed to a stabilizer column 110 to form a first stabilizer column stream 111 that can be output at the top of or adjacent an upper portion of the first stabilizer column 110 and a second stabilizer column stream 112 that can be output at the bottom of or adjacent a lower portion of the second stabilizer column 110.

The stabilizer column 110 can operate at a pre-selected stabilizer column pressure range. The pre-selected stabilizer column pressure range can be selected so that the stabilizer column 110 can output a suitable first stabilizer column stream 111 to be fed to the scrub column 106 as a reflux for the scrub column 106. The stabilizer column operational pressure range can be selected so that it is lower than the operational pressure range of the scrub column 106. In some embodiments, the pre-selected stabilizer column pressure range can be between 15 bara and 30 bara, for example. Other embodiments may utilize another suitable pressure range for the pre-selected stabilizer column pressure range to meet a particular set of design criteria.

In embodiments or implementations where it is desired to maximize the liquid fraction of overhead product from the stabilizer column 110, (e.g. the flow of stream 114 divided by the flow of stream 116), the stabilizer column 110 can be operated at as high a pressure as possible. However this operational pressure for the stabilizer column 110 can be limited by the maximum feasible operating temperature of the stabilizer column reboiler 110A to prevent coke formation since the operating temperature of the reboiler 110A can increase with pressure. In some embodiments this maximum temperature for the stabilizer column reboiler 110A can be 200° C. or around 200° C. (e.g. 185° C. to 205° C.). However, the maximum operating pressure of the scrub column 110 can depend on the composition of the stabilizer bottom product (e.g. second stabilizer column stream 112), which can vary based on the composition of the feed 100 and/or the composition of the second scrub column stream 108 fed to the stabilizer column 110. In some embodiments, an operational pressure for the stabilizer column 110 of between 30 bara and 15 bara can often be utilized to help provide a configuration that facilitates a maximization of the liquid fraction of the overhead product from the stabilizer column 110. However, other operational pressure ranges may also be utilized in different embodiments based on anticipated stabilizer column feed composition and the composition of the second stabilizer column stream 112.

The stabilizer column 110 can include a reboiler 110A that can be positioned and configured to strip methane and ethane from a second stabilizer column stream 112 from the stabilizer column 110 or bottom of the stabilizer column 110 so that the stripped methane and ethane can be returned to the stabilizer column 110 and the second stabilizer column stream 112 can be output as a stream comprising mostly heavy hydrocarbons with a relatively small amount of methane and ethane therein. In some embodiments, the second stabilizer column stream 112 can include between 0 mol % methane and 3 mol % methane, and between 0 mol % ethane and 3 mol % ethane. The remaining portion of the second stabilizer column stream 112 can include heavy hydrocarbons, and possibly also trace amounts of other impurities from the feed 100 (e.g. trace amounts of propane, between 0 mol % butane and 3 mol % butane, etc.). In some embodiments, the second stabilizer column stream 112 can comprise between 100 mol % and 95 mol % heavy hydrocarbons or between 90 mol % and 100 mol % heavy hydrocarbons.

The first stabilizer column stream 111 can comprise mostly lighter hydrocarbons (e.g. methane, ethane, propane, and butane) or only comprise such lighter hydrocarbons. For example, in some embodiments the first stabilizer column stream 111 can include between 15 mol % and 40 mol % methane, between 10 mol % and 40 mol % ethane, between 10 mol % and 40 mol % propane, and between 5 mol % and 15 mol % butane. Other embodiments can be configured to utilize other constituent concentration ranges for the lighter hydrocarbons.

The first stabilizer column stream 111 can be fed to a first stabilizer stream cooling device 142. This cooling device can be an ambient air heat exchanger, a chiller, or other type of suitable cooling device for cooling the first stabilizer column stream 111 to a pre-selected phase separator feed temperature that can be within a suitable pre-selected phase separator feed temperature range. The cooled first stabilizer column stream 111 can include liquid and gas and can be fed to a phase separator 146, which can output a vapor stream 116 and a liquid stream 113.

In some embodiments, the vapor stream 116 can include between 15 mol % and 40 mol % methane, between 10 mol % and 40 mol % ethane, between 10 mol % and 40 mol % propane, and between 5 mol % and 15 mol % butane. The liquid stream 113 can include between 0 mol % and 10 mol % methane, between 5 mol % and 25 mol % ethane, between 15 mol % and 40 mol % propane, and between 20 mol % and 50 mol % butane. Other embodiments can be configured to utilize other constituent concentration ranges of the lighter hydrocarbons for the vapor stream 116 and the liquid stream 113.

The liquid stream 113 can be split so that a first portion 114 of the liquid stream is fed to the first heat exchanger 118 and/or a reflux accumulation vessel 120 for use in forming the scrub column reflux and a second portion 115 is fed to an upper section of the stabilizer column 110 as a reflux stream for the stabilizer column 110. A pump 144 can be positioned to facilitate the feeding of the first and second portions 114 and 115 of the liquid stream 113 to the stabilizer column 110 and the reflux accumulator vessel 120.

The first portion 114 of the liquid stream 113 output from the phase separator 146 can be fed to the heat exchanger 118 with the vapor stream 116 so that these streams can be distributed together through the heat exchanger 118 and the vapor is cooled to a liquid form so that the combined vapor stream 116 and first portion 114 of the liquid stream 113 can form the scrub column reflux output from the heat exchanger 118 as a scrub column reflux stream 148. The scrub column reflux stream 148 can comprise liquid or be a liquid and can be fed to the reflux accumulator vessel 120 for storage therein and subsequently fed from the reflux accumulator vessel 120 to an upper portion of the scrub column 106 as a scrub column reflux feed stream 124. A scrub column reflux feed pump 122 can be configured to facilitate the flow of the scrub column reflux feed stream 124 from the reflux accumulator vessel 120 to the upper portion of the scrub column 106. In some embodiments, the reflux accumulator vessel 120 can be positioned, sized, and configured to help protect the scrub column reflux feed pump 122 to avoid cavitating the pump.

The first scrub column stream 104 can also be passed through the first heat exchanger 118 to function as a cooling medium therein. The warmed first scrub column stream 104 can be output from the first heat exchanger 118 as a treated feed stream 126 for being fed to an NGL recovery plant or an LNG plant.

The treated feed stream 126 can be output at a pre-selected LNG plant feed temperature or other suitable temperature within a pre-selected treated feed stream temperature range. In some embodiments, the pre-selected treated feed stream temperature range can be between 0° C. and 40° C., or between −10° C. and 25° C., or another suitable range. The treated feed stream 126 can also be at a pre-selected treated feed stream pressure that is within a pre-selected treated feed stream pressure range. The pre-selected treated feed stream pressure range can be from 50 bara to 60 bara, 40 bara to 65 bara, or another suitable pressure range. The pre-selected treated feed stream pressure can be an elevated pressure suitable for feeding the treated feed stream to a downstream LNG plant or liquefaction plant process. Such an elevated pressure can provide improved downstream operational flexibility and also permit downstream operations to occur more efficiently and at a lower cost (e.g. by reducing the compression duty and compressor arrangement needed for such processing, etc.).

In other embodiments, the cooling medium flow 134B can be provided to cool the first scrub column stream 104 so this stream can be output from the first heat exchanger 118 as a treated feed stream 126 that is at a lower pre-selected treated feed stream temperature range (e.g. a range of less than −10° C., between −20° C. and −100° C., or another suitable range). Such cooling can be provided so that the first scrub column stream 104 can be cooled in addition to cooling the first portion 114 of the liquid stream 113 for being mixed with the vapor stream 116 as well as the first portion 128 of the feed.

It should be appreciated that conduits, including valves and other conduit elements can be positioned to facilitate the flow of streams and/or portions of streams from one element of the process or apparatus to another. For example, a heat exchanger output conduit can be positioned between the heat exchanger 118 and the scrub column 106 to convey the first portion 128 of the feed output from the heat exchanger 118 to the scrub column 106. As another example, a second portion conduit and third portion conduit can be positioned between the feed conduit through which the feed 100 passes and the scrub column 106 to feed the second and third portions of the feed to the scrub column 106. As another example, a stabilizer column feed conduit can be positioned between the stabilizer column feed cooler 140 and the stabilizer column 110 to convey the cooled second scrub column stream 108 from the stabilizer column feed cooler 140 to the stabilizer column 110 and there can be a stabilizer column cooler feed conduit positioned between the scrub column and the stabilizer column feed cooler 140 to feed the second scrub column stream 108 to the stabilizer column feed cooler 140.

In yet other examples, there can be a first stabilizer column feed conduit positioned between the first stabilizer stream cooling device 142 and the stabilizer column 110 to convey the first stabilizer column stream 111 to the first stabilizer stream cooling device 142. There can also be a phase separator feed conduit positioned between the first stabilizer stream cooling device 142 and the phase separator 146 to feed the cooled first stabilizer column stream to the phase separator 146. A first vapor stream conduit can be positioned between the phase separator 146 and the heat exchanger 118 to feed the first vapor stream 116 from the phase separator 146 to the heat exchanger 118. Also, a first portion of the liquid stream conduit can be positioned between the phase separator 146 and the heat exchanger 118 to feed the first portion 114 of the liquid stream 113 to the heat exchanger 118 for being mixed with the vapor stream 116 and fed through the heat exchanger 118. There can also be a scrub column reflux accumulator feed conduit positioned between the reflux accumulator vessel 120 and the heat exchanger 118 so that the scrub column reflux stream 148 is fed from the heat exchanger 118 to the reflux accumulator vessel 120. Additionally, there can be a stabilizer column reflux conduit positioned between the stabilizer column 110 and the phase separator 146 so that the second portion 115 of the liquid stream 113 can be fed to the stabilizer column 110.

In yet another example, there can be a scrub column reflux feed conduit positioned between the reflux accumulator vessel 120 and the scrub column 106 to feed the scrub column reflux feed stream 124 from the reflux accumulator vessel 120 to the scrub column 106. There can also be a stabilizer column reflux conduit positioned between the phase separator 146 and the stabilizer column 110 to feed the second portion 115 of the liquid stream 113 from the phase separator 146 to the stabilizer column 110. As discussed above, one or more pumps can be positioned in communication with one or more of the conduits to help drive a flow of fluid to different elements (e.g. a stabilizer column reflux driving pump 144 and a scrub column reflux fluid driving pump 122, etc.).

FIG. 2 illustrates an exemplary process for treating a feed gas that comprises methane. Embodiments of the process can facilitate removal of heavy hydrocarbons from the feed gas. An embodiment of the apparatus described herein can utilize an embodiment of this process.

In a first step S1, a feed 100 can be fed to the scrub column 106 and a vapor stream can be output from the scrub column 106 as a first scrub column stream 104. In some embodiments, the first scrub column stream 104 can be fed to a heat exchanger 118 for cooling of at least a portion of the feed 100 to the pre-selected scrub temperature. A lower second scrub column stream 108 can also be output from the scrub column 106 as a liquid or mostly liquid stream. The lower second scrub column stream 108 output from the scrub column 106 can be fed to a stabilizer column 110. The lower second scrub column stream 108 can include heavy hydrocarbons having five or more carbon atoms (e.g. in some embodiments, the second scrub column stream 108 can comprise between 30 mol % and 50 mol % heavy hydrocarbons or between 20 mol % and 40 mol % heavy hydrocarbons).

The scrub column 106 can operate at a pre-selected scrub column operating pressure that is higher than a pre-selected stabilizer column operating pressure. For example, in some embodiments the scrub column 106 can operate in a pressure range of 45 bara to 65 bara and the stabilizer column 110 that receives the second scrub column stream 108 can operate at a pre-selected stabilizing column pressure in a range of 15 bara to 30 bara.

In a second step S2, the stabilizer column 110 can produce a first stabilizer column stream 111 and a portion of this first stabilizer column stream 111 can be fed to the heat exchanger 118 to be cooled therein and subsequently fed to a scrub column as a reflux stream 124 (e.g. the cooled portion of the first stabilizer column stream 11 can be split via a phase separator 146 so that portions of this stream are cooled and fed to an accumulator vessel 120 and subsequently fed as a scrub column reflux feed stream 124 to the scrub column 106). A second stream comprising heavy hydrocarbons of five or more carbon atoms can also be output as a second stabilizer column stream 112 to facilitate removal of the heavy hydrocarbons from the treated feed 126 that is output by the apparatus 1 and fed to an LNG plant or NGL recovery plant for undergoing liquefaction.

In some embodiments, in the second step S2 a portion of the first stabilizer column stream 111 can be cooled to a phase separator feed temperature and fed to a phase separator 146 to form a vapor stream 116 and a liquid stream 113. The liquid stream 113 can be split into a first portion 114 that is fed to the heat exchanger 118 to be used as reflux for the scrub column 106 and a second portion 115 that is fed to the stabilizer column 110 as a reflux stream for the stabilizer column 110.

Embodiments of the process can also include additional steps. For instance, the process can include a third step S3 in which the portion of the first stream output from the stabilizer column 110 is cooled to form the scrub column reflux and fed to the scrub column 106 (e.g. the vapor stream 116 and/or the first portion 114 of the liquid stream 113 output from the phase separator 146 can be cooled via heat exchanger 118 to form the scrub column reflux). The formed scrub column reflux can also be fed to the scrub column 106 via a scrub column reflux feed pump 122 and/or reflux accumulator vessel 120 as discussed above.

As another example, at least a portion of the feed 100 can be cooled to a pre-selected scrub temperature via a heat exchanger 118 and fed to a scrub column 106 for removal of heavy hydrocarbons having five or more carbons (e.g. pentane, hexane, etc.). As can be appreciated from the above, this step of the process can include splitting the feed 100 into different portions and cooling the entirety of this feed or a majority of this feed while a third portion 132 (or second portion if no second portion 130 is formed) may not be cooled and may be fed as a lower section feed portion 132A to a lower section of the scrub column 106. In some embodiments, a third portion 132 can be utilized as a heating medium to form a stripping vapor to be fed to a lower section of the scrub column and subsequently mixed with a second portion 130 and/or a first portion 128 and fed to the scrub column 106 such that all the portions of the feed 100 that may be split from the feed 100 are cooled before being fed to the scrub column 106. It should also be appreciated that in embodiments where the second portion 130 is not formed, the third portion 132 that is split from the feed 100 can be considered a second portion of the feed instead of a third portion of the feed.

Embodiments of the process and apparatus described herein can be configured to provide a treated feed stream 126 that is entirely free of heavy hydrocarbons or almost entirely free of such heavy hydrocarbons (e.g. only including a trace amount of heavy hydrocarbons having five or more carbon atoms). The treated feed stream 126 can be provided at a pre-selected treated feed stream pressure that is within a pre-selected treated feed stream pressure range. The pre-selected treated feed stream pressure range can be from 50 bara to 60 bara, 40 bara to 65 bara, or another suitable pressure range that can be selected to provide an elevated pressure for the treated feed stream 126 so that the treated feed stream 126 can be fed to a downstream LNG plant or liquefaction plant process (e.g. liquefier). Such an elevated pressure can provide improved downstream operational flexibility and also permit downstream operations to occur more efficiently and at a lower cost (e.g. by reducing the compression duty and compressor arrangement needed for such processing, etc.).

It should be appreciated that modifications to the embodiments explicitly shown and discussed herein can be made to meet a particular set of design objectives or a particular set of design criteria. For instance, the arrangement of valves, piping, and other conduit elements (e.g., conduit connection mechanisms, tubing, seals, valves, etc.) for interconnecting different units of the apparatus and providing flows of fluid between different elements (e.g., pumps, heat exchangers, cooling devices, chillers, compressors, etc.) can be arranged to meet a particular plant layout design that accounts for available area of the plant, sized equipment of the plant, and other design considerations. As another example, the flow rate, pressure, and temperature of the fluid passed through the various apparatus or system elements can vary to account for different design configurations and other design criteria.

Embodiments of apparatuses for treating gas feeds that comprise methane to remove impurities from the feed, processes for treating gas feeds that comprise methane to remove impurities from the feed, and/or systems for treating gas feeds that comprise methane to remove impurities from the feed can each be configured to include process control elements positioned and configured to monitor and control operations (e.g., temperature and pressure sensors, flow sensors, an automated process control system having at least one work station that includes a processor, non-transitory memory and at least one transceiver for communications with the sensor elements, valves, and controllers for providing a user interface for an automated process control system that may be run at the work station and/or another computer device of the plant, etc.). It should be appreciated that embodiments can utilize a distributed control system (DCS) for implementation of one or more processes and/or controlling operations of an apparatus as well.

As another example, it is contemplated that a particular feature described, either individually or as part of an embodiment, can be combined with other individually described features, or parts of other embodiments. The elements and acts of the various embodiments described herein can therefore be combined to provide further embodiments. Thus, while certain exemplary embodiments of the processes, apparatuses, systems, and methods of making and using the same have been shown and described above, it is to be distinctly understood that the invention is not limited thereto but may be otherwise variously embodied and practiced within the scope of the following claims.

What is claimed is:

1. An apparatus for removal of heavy hydrocarbon impurities from a feed comprising methane gas and hydrocarbons having at least five carbon atoms, the apparatus comprising:

a scrub column positioned and configured to receive the feed and output a first scrub column stream and a second scrub column stream, the second scrub column stream comprising the hydrocarbons having at least five carbon atoms, a stabilizer column positioned downstream of the scrub column to receive the second scrub column stream and configured to output a first stabilizer column stream and a second stabilizer column stream, the second stabilizer column stream comprising the hydrocarbons having at least five carbon atoms, a phase separator positioned to receive the first stabilizer column stream and output a vapor stream and a liquid stream, and a heat exchanger positioned to receive the vapor stream from the phase separator and a first portion of the liquid stream from the phase separator;

wherein the scrub column is positioned such that a portion of the first stabilizer column stream is fed to the scrub column as a scrub column reflux stream;

wherein the portion of the first stabilizer column stream that is fed to the scrub column as the scrub column reflux stream comprises the vapor stream from the phase separator and the first portion of the liquid stream from the phase separator;

wherein the heat exchanger is configured and positioned to cool a first portion of the feed before the feed is fed to the scrub column;

wherein the scrub column is positioned so that a third portion of the feed is passed through a side reboiler of the scrub column to cool that portion of the feed; and wherein the heat exchanger and the scrub column are positioned such that the third portion of the feed cooled in the side reboiler is combined with the first portion of the feed and fed to the scrub column.

2. The apparatus of claim 1, comprising:

a reflux accumulator vessel positioned to receive the scrub column reflux stream, store the scrub column reflux stream, feed the scrub column reflux stream to the scrub column.

3. The apparatus of claim 2, wherein:

the heat exchanger is positioned to receive the first scrub column stream from the scrub column, and cool the scrub column reflux stream before the scrub column reflux stream is fed to the reflux accumulator vessel.

4. The apparatus of claim 1, comprising:

the heat exchanger is positioned to receive the first scrub column stream from the scrub column, and cool the scrub column reflux stream before the scrub column reflux stream is fed to the scrub column.

5. The apparatus of claim 1, wherein the scrub column is positioned so that the third portion of the feed passed through the side reboiler of the scrub column heats liquid from the scrub column to form a stripping vapor, the side reboiler positioned to output the stripping vapor to the scrub column.

6. The apparatus of claim 1, further comprising:

a reflux accumulator vessel positioned to receive the portion of the first stabilizer column stream that is fed to the scrub column, store the scrub column reflux stream, and feed the scrub column reflux stream to the scrub column; and a pump positioned to drive the flow of the scrub column reflux stream from the reflux accumulator vessel to the scrub column;

wherein the stabilizer column is configured to operate at a pre-selected stabilizer column operational pressure range, and the scrub column is configured to operate at a pre-selected scrub column operational pressure range that is greater than the pre-selected stabilizer column operational pressure range.

7. The apparatus of claim 1, wherein:

the heat exchanger is configured and positioned to cool the scrub column reflux stream before the scrub column reflux stream is fed to the scrub column.

8. The apparatus of claim 7, further comprising:

a reflux accumulator vessel positioned to receive the scrub column reflux stream from the heat exchanger, store the scrub column reflux stream, and feed the scrub column reflux stream to the scrub column; and a pump positioned to drive the flow of the scrub column reflux stream from the reflux accumulator vessel to the scrub column;

wherein the stabilizer column is configured to operate at a pre-selected stabilizer column operational pressure range, and the scrub column is configured to operate at a pre-selected scrub column operational pressure range that is greater than the pre-selected stabilizer column operational pressure range.

9. A process for treating a feed gas comprising methane and hydrocarbons having at least five carbon atoms, the process comprising:

providing the feed gas to a scrub column operating at a pre-selected scrub column operational pressure range to output a first scrub column stream and a second scrub column stream from the scrub column, the second scrub column stream comprising the hydrocarbons having at least five carbon atoms;

feeding the second scrub column stream to a stabilizer column operating at a pre-selected stabilizer column operational pressure range to output a first stabilizer column stream and a second stabilizer column stream, the second stabilizer column stream comprising the hydrocarbons having at least five carbon atoms;

providing a portion of the first stabilizer column stream to the scrub column to provide a scrub column reflux stream to the scrub column;

splitting the feed into a first portion, a second portion, and a third portion, feeding the first portion to a heat exchanger positioned upstream of the scrub column, mixing the first portion exiting the heat exchanger with the second portion before providing a stream comprising the first and second portions to the scrub column; and feeding the third portion to a side reboiler to form a stripping vapor, and feeding the stripping vapor to the scrub column, wherein the process comprises mixing the third portion with the second portion and the first portion before the first portion, second portion, and third portion of the feed are fed to the scrub column, the second portion before the first portion, second portion, and third portion of the feed are fed to the scrub column, or the first portion before the first portion, second portion, and third portion of the feed are fed to the scrub column.

10. The process of claim 9, comprising:

feeding the first stabilizer column stream to a phase separator to form a vapor stream and a liquid stream;

feeding the vapor stream and a portion of the liquid stream to a heat exchanger to form the scrub column reflux stream;

feeding the scrub column reflux stream from the heat exchanger to a reflux accumulator vessel; and feeding the scrub column reflux stream from the reflux accumulator vessel to an upper section of the scrub column.

11. The process of claim 10, comprising:

feeding the first scrub column stream to the heat exchanger as a cooling medium to cool the vapor stream and the portion of the liquid stream fed to the heat exchanger to form the scrub column reflux stream.

12. The process of claim 9, wherein the pre-selected scrub column operational pressure range is between 45 bara and 65 bara, and the pre-selected stabilizer column operational pressure range is between 15 bara and 30 bara.

13. The process of claim 9, comprising:

mixing the third portion with the second portion and the first portion before the first portion, second portion, and third portion of the feed are fed to the scrub column.

14. The process of claim 9, wherein the pre-selected stabilizer column operational pressure range is lower than the pre-selected scrub column operational pressure range.

15. The process of claim 9, comprising:

mixing the third portion with the second portion before the first portion, second portion, and third portion of the feed are fed to the scrub column.

16. The process of claim 9, comprising:

mixing the third portion with the first portion before the first portion, second portion, and third portion of the feed are fed to the scrub column.

* * * * *